United States Patent [19]

Marvel

[11] Patent Number: 4,840,618
[45] Date of Patent: Jun. 20, 1989

[54] MEDICAL SAFETY DEVICE

[76] Inventor: Ray D. Marvel, 3206 Highway 92, Hotchkiss, Colo. 81419

[21] Appl. No.: 185,855

[22] Filed: Apr. 25, 1988

[51] Int. Cl.$^4$ ............................................... A61M 5/00
[52] U.S. Cl. .................................... 604/187; 604/192; 604/263
[58] Field of Search ......................... 604/187, 192, 263

[56] References Cited

U.S. PATENT DOCUMENTS 4,485,918 12/1984 Mayer .............................. 604/263 X

FOREIGN PATENT DOCUMENTS 0192453 8/1986 European Pat. Off. ............. 604/187
2586568 3/1987 France ................................. 604/192

Primary Examiner—John D. Yasko
Attorney, Agent, or Firm—Donald W. Erickson; John E. Holder

[57] ABSTRACT

The particular embodiment described herein as illustrative of one form of the invention incorporates a round elongated handle sized for holding in the fisted grip of a person. A shield is positioned on top of the handle and extends radially outwardly therefrom to an extent sufficient to substantially shield the fisted hand of a person gripping the handle. An opening in the center of the shield communicates with a cavity in the handle for receiving a test tube therein. When transferring fluids from a syringe to a test tube, one inserts the test tube into the cavity in the handle and then inserts a syringe needle into the upper end of the test tube with the other hand. If the person performing the operation were to miss the end of the test tube with the needle, the hand of the person holding the device holding the test tube would be shielded from the needle. A ridge on the outer peripheral edge of the shield will pervent a needle from sliding off the edge of the shield should the needle strike the shield.

A sighting window in the handle permits the operator to view the level of fluid transferred into the test tube. An opening on the side of the handle permits the test tube to be contacted from the side of the handle to facilitate its ejection from the cavity in the handle, its being held in the handle while a syringe needle is extracted from the test tube, and the gripping of the handle with the fingers to prevent slippage of the hand from the handle. A small opening in the end of the handle prevents a vacuum from forming between the bottom of the test tube and the bottom of the test tube cavity in the handle.

14 Claims, 1 Drawing Sheet

MEDICAL SAFETY DEVICE

BACKGROUND OF THE INVENTION

1. Field of the Invention

The present invention pertains to a medical safety device and more particularly to an apparatus for providing a safety shield against the inadvertent sticking of a syringe needle into the hand of a person in the process of transferring body fluids from a syringe into a test tube.

2. History of the Prior Art

The medical community in recent years has become increasingly aware of, and concerned about, the transmission of infectious disease and viruses in the laboratory, clinic, and hospital environment where patients carrying such a disease, virus or the like are in physical communication with health care personnel. A recently discovered virus, the human immunodeficiency virus (HIV) has a special affinity for helper T cells and macrophages, which are among the immune system's primary weapons against disease. Its clinical manifestations are diseases that were once rare and it is the known cause of acquired immune deficiency syndrome (AIDS) and AIDS-related complex, a less severe form of the condition. The virus can remain hidden in cells for years before it begins to multiply and destroy the immune system. In the U.S. alone there may be up to 2 million carrying the virus with neither sign or symptom of the illness. Since it may be several years before effective antiviral drugs or vaccines can be developed, it is likely that testing individuals for carrying of the virus will be under more and more demand.

With this onslaught of the AIDS virus as a deadly contaminant to be reckoned with in the health care field has come the accompanying problem of safety in handling patients with any such virus or disease. Since AIDS is one of the strong motivating factors leading to the development of this invention, the background and description of this invention is strongly addressed thereto. As mentioned, one of the most pressing factors relating to the control of AIDS, or any disease for that matter, is detection. Since contamination by the virus can be completed by contact of a carrier's body fluids with sensitive portions of another's body, the chances of contracting the virus are particularly high where people are handling the body fluids of carriers. Such is the case for those testing for the virus by taking body fluid samples with a syringe. Part of the typical process of taking samples of blood for example, is to remove the sample into a syringe by way of a needle injected into the patient and then to transfer the blood sample from the syringe into a test tube. This is typically done by inserting the syringe needle (after the sample has been captured in the syringe) into an evacuated test tube. The test tube, which has its interior under a vacuum, has a rubber stopper or the like at its upper end for maintaining the vacuum. The syringe needle is injected through the top of the stopper and into the evacuated space, whereupon the blood sample is drawn by the lower pressure of the vacuum into the test tube.

The syringe needle is then removed from the stoppered end of the test tube and discarded. It is in this process of transferring the blood from the syringe into the test tube that a danger exists for the person performing the transfer to be injected with the virus. If the person making the transfer were to inadvertently miss the stoppered end of the test tube, the syringe needle could easily contact and pierce the skin of the person performing the transfer or another person holding the test tube. This in itself could cause the virus to be transmitted to the hand of that person.

It is therefore an object of the present invention to provide a new and improved device for preventing the accidental sticking of a person attempting to transfer a body fluid sample from a syringe to a test receptacle.

SUMMARY OF THE INVENTION

With this and other objects in view, the present invention contemplates a safety shield device for safely transferring fluids from a syringe to a test tube while protecting the hand of a person performing the operation from being inadvertently stuck with the syringe needle. The device has an elongated handle with a cavity therein for receiving a test tube. The upper end of the handle has a radially extending shield portion which extends outwardly around the top of the handle to the extent that it substantially covers the hand of a person gripping the handle in an enclosed or fisted hand grip.

A lip is formed around the upper peripheral surface of the shield so that if a syringe needle were to strike the top of the shield, the needle would be prevented from sliding over the edge of the shield into contact with the fist, arm, or other body part of a person gripping the handle. A sight window on the handle permits viewing of a test tube inserted into the handle cavity by way of an opening in the top of the shield and communicating with the cavity in the handle. An elongated opening in the side of the handle permits a person to engage the side of the test tube in the handle and apply frictional pressure to the side of the test tube to assist in the removal of the test tube from the handle cavity. This elongated opening also provides a means for gripping the handle to prevent its slipping from the hand. Also a series of vertical ridges is formed on the handle to further facilitate gripping. A small opening in the bottom of the handle is provided to prevent a vacuum from forming between the bottom of a test tube in the cavity and the bottom of the handle cavity.

BRIEF DESCRIPTION OF THE DRAWINGS

For a more complete understanding of the present invention, and for further objects and advantages thereof, reference may now be had to the following description when taken in conjunction with the accompanying drawings in which.

DETAILED DESCRIPTION OF THE PREFERRED EMBODIMENTS

Figure 1:
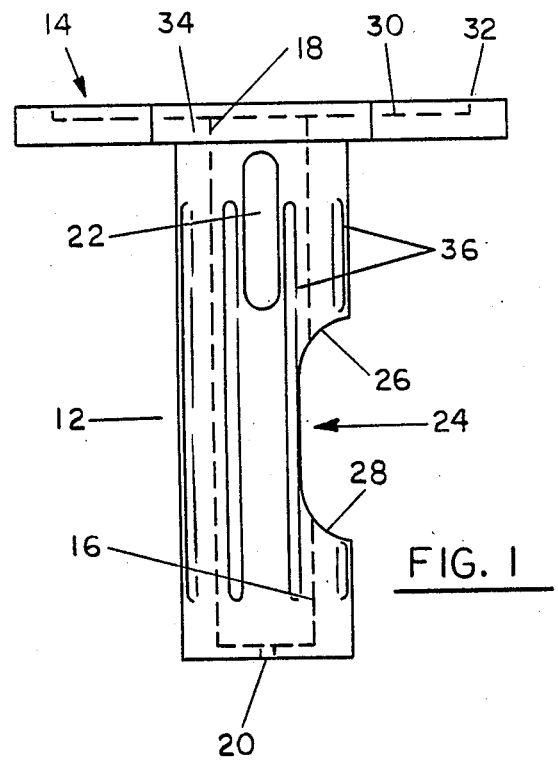
FIG. 1 is a side elevational view of the hand shield device for safely transferring fluids from a syringe to a test tube in accordance with the present invention.

Referring first to FIG. 1 of the drawings, the safety shield apparatus is shown having an elongated handle portion 12 which is shown to be cylindrical in shape and having a disc-like shield portion 14 extending radially outwardly from the upper end of the handle portion. The handle portion 12 has a cylindrical cavity 16 formed therein extending from a top opening 18 in the shield portion 14 to the bottom of the handle portion. A small opening 20 at the bottom of the cavity 16 communicates the bottom end of the cavity with the bottom outside surface of the handle portion. An elongated opening 22 is formed in the side wall of the handle portion 12 to provide a window for viewing the level of fluids in a test tube inserted into the cavity 16. If the handle 12 were made of a transparent material, this visual function would be provided by the material itself and such viewing window would be unnecessary. However, for various reasons one of which is appearance, an opaque material for constructing this apparatus may be desirable and in such event, the window 22 together with a second wall opening in the side of the handle would provide a viewing window throughout the length of the cavity.

The primary functions, however, of the second opening 24 are to provide a means for contacting the side wall of a test tube within the cavity 16 and pushing upwardly thereon to lift the test tube up out of the cavity without pulling on the top of the test tube, and also to provide a means for holding the test tube with either the gripping fingers of the hand or with the thumb to hold downwardly on the test tube while the syringe needle is being extracted from the stoppered end of the test tube. In addition, when the hand is gripped about the handle the second opening is sized lengthwise to permit the middle and ring fingers to span across the relative flatness of the opening to facilitate gripping of the handle to prevent slippage.

The shape of the opening 24 with the top and bottom ends 26 and 28 respectively of the opening 24 being beveled, and the cut for the opening being straight across the wall of the handle as shown in FIG. 1, facilitate the use of the person holding the apparatus to apply thumb pressure to the side of a test tube and slide it upwardly, to hold down on the test tube when removing the syringe needle and gripping of the handle with the fingers of the hand. The bottom hole 20 provides a means for breaking a vacuum which may form between the bottom of the test tube and the bottom of the cavity, in that the cavity 16 is sized to fit snugly about the test tube while at the same time permitting the test tube to slide in and out of the cavity. This mating fit between the test tube and cavity will require a rather precise dimensioning of the cavity. The shield portion 14, on the upper end of the handle, has a recessed surface 30 on top of the disc which forms a peripheral shoulder portion 32 projecting upwardly from around the entire outer edge of the shield portion. A plurality of flat portions 34 are formed on the outer edge of the disc 14. A series of longitudinal ridges 36 are formed on the outer surface of the handle 12 to further facilitate gripping of the handle.

Figure 2:
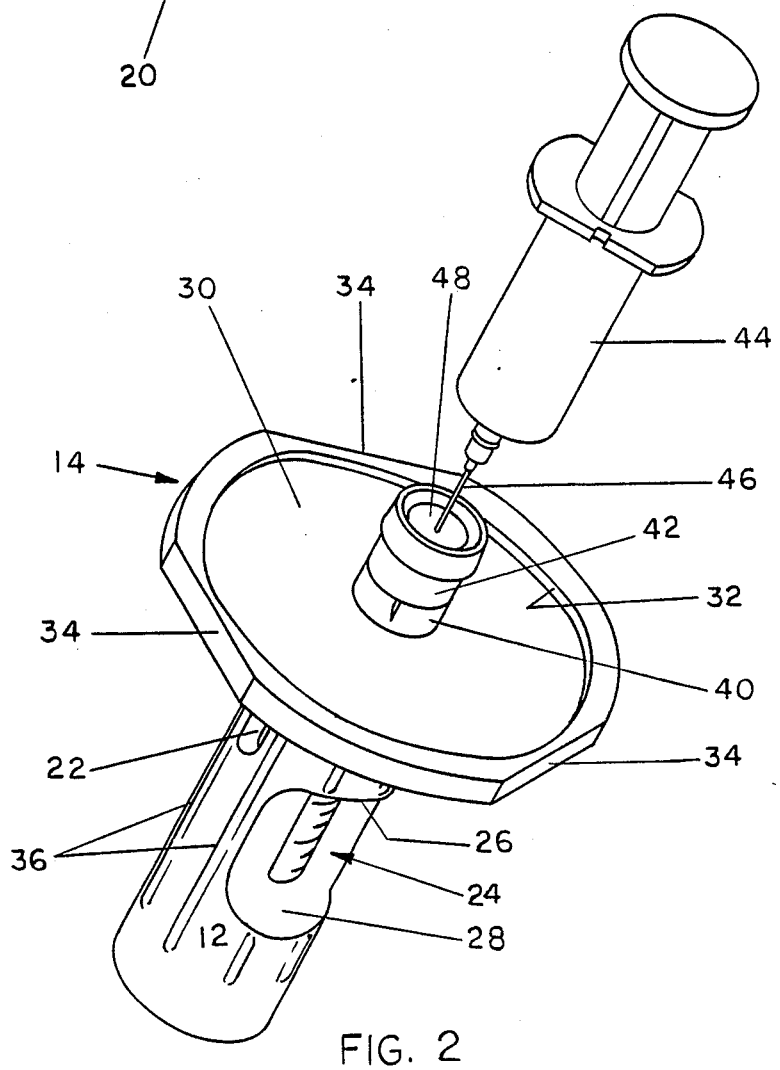
FIG. 2 is a perspective view of the hand shield device of FIG. 1 showing a syringe injected into a test tube held in the safety device.

Referring now to FIG. 2 of the drawings the apparatus is shown having a test tube 40 received within the cavity 16 and projecting upwardly through opening 18 (FIG. 1) in the top of shield 14. The test tube 40 has a rubber stopper 42 closing off its upper end for maintaining a vacuum within the test tube and for capturing any fluids received within the test tube. A syringe 44 is shown having a needle 46 inserted into the concave upper end 48 of the stopper 42 for transferring fluids to the interior of the syringe and for transferring fluids from the interior of the syringe into the test tube 40.

In the operation of taking a body fluid sample from a patient by means of a syringe and needle, the sample body fluid taken from a patient is then transferred, usually on the spot where the sample is taken, into a test tube for transfer to a laboratory environment for subsequent test and/or analysis. In this process of taking a sample and transferenace to a test tube, there is a danger that when the operator is injecting the syringe needle 46 into the stoppered end 48 of the test tube, that the tip end of the needle 46 will slip off the edge of the upper end of the test tube and strike the hand of the person holding the test tube. This could cause the needle 46 to penetrate the skin of the operator holding the test tube and thus infect the operator with any disease, virus or the like which the patient, from whom the sample was taken, might have. Therefore, in the use of the apparatus of the present invention as shown and described with respect to FIGS. 1 and 2 of the drawings, this danger is avoided. This is accomplished as follows: when a body fluid sample is taken from a patient into a syringe 44, a test tube to which the sample is to be transferred, is inserted into the opening 18 on top of the shield 14 and pushed into the cavity 16 within handle portion 12 of the apparatus until the bottom of the test tube seats on the bottom of the cavity 16 in the handle. The depth of the cavity is dimensioned such that the top of the test tube will project upwardly above the shield 14 when the test tube is seated in the cavity. At this time, the operators will insert the needle 46 of the syringe into the upper end 48 of the test tube stopper 42 and through the stopper to project into the test tube below the stopper. If the test tube is of the vacuum type, the sample will be drawn into the test tube. When it appears that all the sample has been withdrawn from the syringe, or by observation through the window 22 it appears that the test tube is full of fluid, the needle 46 is withdrawn from the stopper 42 and usually the syringe is discarded into a receptacle. In order to prevent the test tube from raising in the cavity 16 when the syringe needle is withdrawn from the stoppered end 42 of the test tube, the fingers or thumb of the operator are placed against the test tube through the window 24 to hold the test tube in place.

The apparatus may then be positioned on a table surface or the like on its side with one of the flats 34 on the rim of the shield 14 preventing the apparatus from rolling off. Alternatively or thereafter, the test tube may be removed from the cavity 16 by applying upward pressure usually with the thumb or a finger to the side of the test tube by means of the opening 24. The manner in which the opening is cut in the side of the handle wall permits easy access of the thumb or finger to the side of the test tube to push upwardly on the tube and move the tube up and out of the cavity 16. The other hand then may grasp the upper end of the test tube for transfer to some other place.

If during the process of transferring the sample of body fluid as described above, when the operator attempts to push the syringe needle into the upper end 48 of the test tube stopper, the needle should slip off the end of the test tube and downwardly, relative thereto, the needle will strike the top surface 30 of the shield 14 instead of the operator's hand and should the needle slide on the surface 30, the upwardly projecting edge portion 32 will prevent the needle from sliding off the edge of shield 14. In this manner the operator's hand is completely protected from the likelihood of an inadvertent stab being made by a contaminated needle into the hand or arm of the operator.

While a particular embodiment of the present invention has been shown and described, it is apparent that changes and modifications may be made without departure from this invention in its broader aspects, and therefore the aim in the appended claim is to cover all such changes and modifications as held within the true spirit and scope of this invention.

What is claimed is:

1. Apparatus for providing a safety shield to an operator in the process of transferring body fluids from a syringe to a test container which comprises:

a handle for holding the safety shield in the hand of an operator, said handle having the form of an elongated, substantially cylindrical member with a longitudinal dimension which is sufficient to extend transversely across the palm of the operator's hand and having formed therein a longitudinal cavity within the substantially cylindrical member that is long enough to receive the greater part of a test container lengthwise, said cavity being sized for securely holding the test container and a shield extending radially outwardly from the upper end of the handle to a distance such that when the handle is grasped within the operator's palm to form a clenched fist about the handle, the bottom surface of the shield substantially covers the upper side of the clenched fist.

2. The apparatus of claim 1 wherein the upper side of the shield has an upwardly extending shoulder about the outer edge thereof.

3. The apparatus of claim 1 wherein the shield is a substantially flat disc having at least one flat surface on its outer circumferential edge.

4. Apparatus for providing a safety shield to an operator in the process of transferring body fluids from a syringe to a test container which comprises:

a handle for holding the safety shield in the hand of an operator, said handle having the form of an elongated, substantially cylindrical member with a longitudinal dimension which is sufficient to extend transversely across the palm of the operator's hand and having formed therein a longitudinal cavity within the substantially cylindrical member that is long enough to receive the greater part of a test container lengthwise, said cavity being sized for securely holding the test container and a shield extending laterally outward from the upper end of the cavity in the handle, and further including an opening in the side of the cylindrical member for communicating the interior of the cavity within the handle to the outside surface of the handle for permitting contact with a test container in the cavity from the side of the cylindrical member.

5. The apparatus of claim 4 including means in the side of the handle for observing at least a portion of a test container when positioned within the cavity.

6. The apparatus of claim 1 wherein the cavity has means forming a top opening for receiving the test container and further including an opening in the bottom of the cavity opposite the top opening.

7. Apparatus for facilitating the holding of a test tube in a person's hand while transferring fluids from a syringe which has a needle for taking and dispensing body fluids into and from the syringe and for protecting the person's hand from contact by the needle which comprises:

an elongated handle sized to be held in a person's hand with the palm and fingers closed about the handle to create the form of a fist;

a cavity formed within the handle and sized to receive a test tube, said cavity being in a cylindrical shape having an open upper end, said cylindrical cavity being sized to matingly receive and securely hold the test tube and having a length such that when the test tube is fully inserted into the cavity, the upper end of the test tube projects above the upper open end of the cavity in the handle; and a shield on said handle for shielding a hand closed about the handle when the contents of a syringe are transferred into the test tube.

8. The apparatus of claim 7 wherein the shield is a disc extending radially from the upper end of the handle for shielding the fist which is clasped about the handle when the apparatus is held in a person's hand, with the fisted hand being positioned below the disc and the upper end of the cavity opening above the disc.

9. The apparatus of claim 7 having an opening in the side wall of the handle communicating the interior of the cavity with the exterior of the handle, such side opening being sized to permit finger pressure to be applied to the test tube and to facilitate gripping of the handle.

10. The apparatus of claim 8 having means extending upwardly from the outer peripheral edge of the disc to prevent a syringe needle from sliding off the edge of the disc.

11. The apparatus of claim 7 having an opening in the bottom of the handle for preventing a vacuum from forming between the bottom of the cavity and the bottom of a test tube inserted into the cavity.

12. The apparatus of claim 7 having means for viewing the test tube when the test tube is inserted into the cavity to determine the level of fluid in the test tube.

13. The apparatus of claim 8 wherein the disc shield has at least one flat surface formed on the outer peripheral edge of the disc to prevent the apparatus from rolling about the disc if the apparatus is laid on its side on a supporting surface.

14. The apparatus of claim 7 having vertical ridges on the outer surface of the handle for facilitating gripping of the handle by the hand.

* * * * *